United States Patent
Legay et al.

(10) Patent No.: US 9,566,438 B2
(45) Date of Patent: Feb. 14, 2017

(54) ACTIVE IMPLANTABLE MEDICAL DEVICE FOR NEURAL THERAPY WITH STOCHASTIC STIMULATION OF THE VAGUS NERVE

(71) Applicant: SORIN CRM S.A.S., Clamart (FR)

(72) Inventors: Thierry Legay, Fontenay les Briis (FR); Hervé Blumstein, Mévoisins (FR)

(73) Assignee: SORIN CRM SAS, Clamart (FR)

( * ) Notice: Subject to any disclaimer, the term of this patent is extended or adjusted under 35 U.S.C. 154(b) by 182 days.

(21) Appl. No.: 14/301,127

(22) Filed: Jun. 10, 2014

(65) Prior Publication Data
US 2014/0364923 A1    Dec. 11, 2014

(30) Foreign Application Priority Data

Jun. 11, 2013   (FR) ...................................... 13 55384

(51) Int. Cl.
*A61N 1/08*    (2006.01)
*A61N 1/36*    (2006.01)

(52) U.S. Cl.
CPC ....... *A61N 1/36178* (2013.01); *A61N 1/36053* (2013.01); *A61N 1/36114* (2013.01)

(58) Field of Classification Search
CPC ............ A61N 1/36128; A61N 1/36146; A61N 1/36167; A61N 1/36053; A61N 1/36114; A61N 1/36178
USPC .............................. 607/9, 72, 73, 17, 25, 62
See application file for complete search history.

(56) References Cited

U.S. PATENT DOCUMENTS

| | | | |
|---|---|---|---|
| 7,076,308 B1 | 7/2006 | Overstreet et al. | |
| 2007/0027486 A1 | 2/2007 | Armstrong | |
| 2008/0065158 A1* | 3/2008 | Ben-Ezra | A61N 1/36071 607/2 |
| 2011/0009923 A1 | 1/2011 | Lee | |
| 2011/0190569 A1 | 8/2011 | Simon et al. | |
| 2013/0066392 A1 | 3/2013 | Simon et al. | |

FOREIGN PATENT DOCUMENTS

EP    1 897 586    3/2008

OTHER PUBLICATIONS

Preliminary Search Report for French Patent Application No. FR1355384, dated Oct. 8, 2013, 2 pages.

* cited by examiner

*Primary Examiner* — Edward Moran
*Assistant Examiner* — Michael Carey
(74) *Attorney, Agent, or Firm* — Foley & Lardner LLP

(57) ABSTRACT

This device comprises a generator producing bursts (Si) of N pulses (I) of VNS stimulation generated in succession during respective periods of activity (TON) separated by intermediate periods of inactivity (TOFF) during which no stimulation is issued. Stochastic modulation circuitry controls the delivery of the bursts of each of the N pulses of each VNS burst by selective inhibition or not, of the generation of each of the VNS pulses depending on the result of a respective randomization. The number of VNS pulses of each burst is thus randomly varying, and thus the VNS stimulation energy of this burst and the interval between successive pulses, which counteract the appearance of a physiological compensation loop.

19 Claims, 2 Drawing Sheets

ACTIVE IMPLANTABLE MEDICAL DEVICE FOR NEURAL THERAPY WITH STOCHASTIC STIMULATION OF THE VAGUS NERVE

CROSS-REFERENCE TO RELATED APPLICATION

This application claims the benefit of and priority to French Patent Application No. 1355384, filed Jun. 11, 2013. French Patent Application No. 1355384 is hereby incorporated by reference in its entirety.

BACKGROUND

The invention relates to "active implantable medical devices" as defined by Directive 90/385/EEC of 20 Jun. 1990 of the Council of the European Communities, specifically implants for delivering therapies of stimulation of the vagus nerve, called VNS therapies (Vagus Nerve Stimulation). The stimulation of the nervous system is recognized as a possibility for treating many disorders such as epilepsy therapy, pain, heart failure, sleep apnea, obesity, or others.

The devices used for this purpose typically include a lead equipped with an electrode implanted on the vagus nerve and a generator supplying VNS pulses on this electrode. If the vagus nerve is to be stimulated further in synchronism with the heartbeat, the apparatus may further include one or more cardiac leads for collecting of depolarization waves of the myocardium.

In some devices, the VNS therapy is to add an arbitrary signal (VNS pulses) overlapping signals naturally conveyed by the nervous system. This stimulation of the vagus nerve may act in an efferent manner, carrying the pulses to the organ, or act in an afferent manner (e.g., pulses are sent to the brain to affect the central nervous system). The arbitrary signal including VNS pulses may be interpreted by the central nervous system as a solicitation that the central nervous system will try to compensate to oppose, and thereby preventing production of the expected effects.

The profile of stimulation of the vagus nerve consists of bursts (or trains) of repetitive pulses produced during a period known as "activity", followed by an "inactive" period during which the stimulus is no longer delivered. The energy of each burst is determined by the width, amplitude, number, frequency, and pulse morphology, parameters that all are adjusted by appropriate setting of the VNS pulse generator.

The problem addressed by the invention is related to the fact that if neuronal therapy by VNS stimulation is effective at the beginning of its application, the VNS stimulation often seems to lose its effectiveness over time (e.g., a few weeks) due to compensation phenomena coming from the creation of a loop of physiological control.

SUMMARY

The basic idea of the invention includes applying VNS stimulation to a patient by modulating every burst of pulses so as to induce variations in the energy delivered by the burst, and the interval between pulses.

This artificially induced variability of VNS stimulation may be of a stochastic type, that is to say it is non-deterministic, in order to avoid compensation of the excitation of the vagus nerve by a physiological loop involving the central nervous system, a phenomenon which would reduce the beneficial effects resulting from the VNS therapy.

Thus, U.S. 2007/0027486 A1 discloses a VNS generator wherein the energy delivered is modulated from one pulse to the next or from one burst to the next, by randomly varying the width and the amplitude of the pulses and the time interval between successive pulses, or the intensity of the current delivered by the pulse. However, such a system requires complex control systems of the various operating parameters of the generator (current, timing, etc.) and makes it difficult to control the average energy delivered to the patient, beyond the random modulation.

According to the invention, the stochastic modulation is achieved by controlling, during each emission of a pulse burst, the delivery of each pulse of this burst by a random or pseudo-random function of the "heads or tails" type applied to the delivery of each of such pulses of each burst, thus avoiding any potential compensation by a physiological mechanism.

The VNS energy delivered to the nerve for each cardiac cycle will thus randomly vary, theoretically from zero (no pulse delivered) to the maximum (all of the initially planned pulses of the burst being delivered).

Accordingly, for each burst of pulses, a different, not predictable, energy is applied to the vagus nerve which consequently causes an unexpected modulation of the VNS therapy, avoiding a physiological loop to systematically oppose to it. The interval between two successive pulses actually delivered also unpredictably varies.

In this method, a long-lasting effect of the neuronal therapy can be obtained, for the compensation by a physiological control loop is no longer possible or made much more difficult.

More specifically, the invention discloses an active implantable medical device for neuronal stimulation therapy of the vagus nerve, such as disclosed in the US2007/0027486 A1 cited above. It includes a generator capable of producing bursts of N VNS stimulation pulses generated in succession during respective periods of activity, the periods of activity being separated by intermediate periods of inactivity during which no stimulation is delivered. It also includes methods of stochastic modulation of the bursts, adapted to separately control the delivery of each of the N VNS pulses of each burst so as to randomly vary the VNS stimulation energy contained in this burst and the interval between successive pulses and thus counteract the appearance of a physiological compensation loop.

The methods of stochastic modulation may include a pseudo-random binary generator of "heads or tails" type, outputting a random binary result '0' or '1' for each VNS pulse likely be applied, and inhibiting methods, able to respectively control the inhibition or authorization of delivery of the VNS pulse based on said random binary outcome for each pulse of each of the successive bursts, so as to randomly vary the number of VNS pulses delivered in a burst.

In this method, the number of VNS pulses delivered in a burst randomly varies and consequently varies the VNS stimulation energy contained in this burst and the interval between successive pulses, which counteracts against the appearance of a physiological compensation loop.

Preferably, the respective amplitudes of the pulses delivered by the VNS generator are all equal, as well as their respective widths, and the respective time intervals separating the instants of application of two successive VNS pulses delivered by the generator during each burst, whether their delivering by the generator is or is not inhibited by the methods of stochastic modulation.

The repetition frequency of VNS pulses delivered by the generator may in particular be between 15 and 50 Hz.

The duration of the periods of activity is preferably constant, and between 15 and 60 seconds. Similarly, the duration of the inactivity periods is preferably constant and is between 2 and 10 minutes.

DETAILED DESCRIPTION

Embodiments described herein may include a microprocessor provided with programmable circuits for shaping and delivering stimulation pulses to implanted electrodes. In some embodiments, the method of the invention is implemented primarily by software, by appropriate algorithms executed by the microprocessor and/or another microcontroller or a digital signal processor.

For the sake of clarity, the various processing applied will be broken down and diagrammed by a number of different functional blocks in the form of interconnected circuits, however this representation is only illustrative, these circuits including common elements and in practice corresponding to a plurality of functions performed by single overall software.

Figure 1:
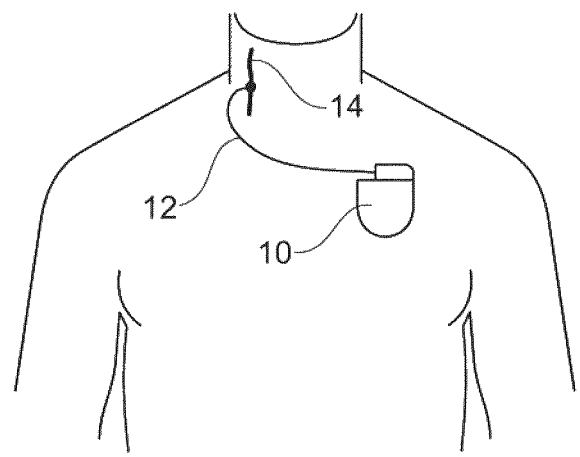
FIG. 1 is an overview presentation of the device of the invention, showing the generator, the vagus nerve wave and the used lead.

In FIG. 1, the reference 10 designates the housing of a vagus nerve stimulation implantable generator. This stimulation is delivered by a lead 12 bearing at its distal portion an electrode implanted on the vagus nerve 14 and able to stimulate the latter by application of pulse bursts produced by the generator 10.

Figure 2:
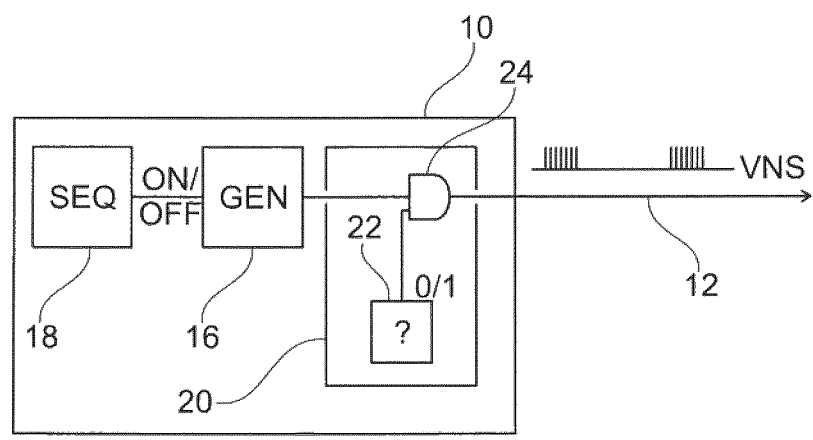
FIG. 2 is a block schematic view corresponding to the main features of the generator of the device of the invention.

FIG. 2 schematically illustrates the main features of the generator 10 of the device of the invention.

The device of the invention includes a generator circuit 16 adapted to produce VNS pulse bursts delivered to the vagus nerve through the lead 12. The generator circuit 22 is controlled by a sequencer circuit 18, which controls the generator 16 so as to deliver VNS pulse bursts for "activity" periods (TON), interspersed with "inactivity" periods (TOFF).

The repetition frequency of the pulses produced by the generator 16 is typically between 15 and 50 Hz, and the periods of activity and inactivity defined by the sequencer circuit 18 are typically between 15 to 60 seconds for TON and between 2 to 10 minutes for TOFF.

A representative example, of course non-limiting, of the invention is to generate pulses at a repetition rate of 30 Hz for a period TON=30 seconds followed by a period of inactivity TOFF=5 minutes.

Figure 3A:
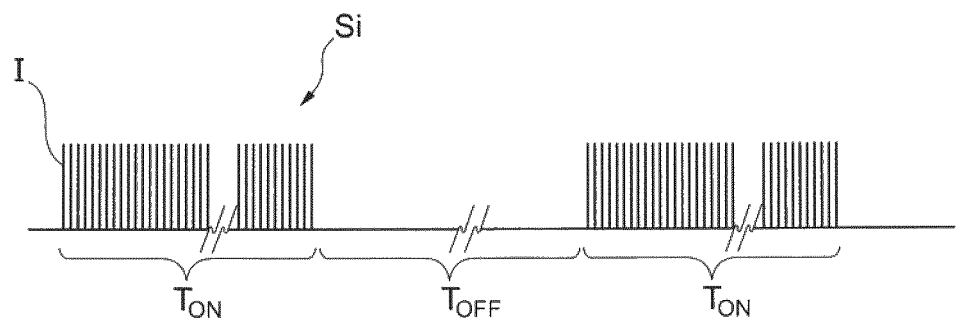
FIGS. 3a to 3c disclose timing diagrams showing on a same temporal line a succession of two bursts of VNS pacing pulses.

FIG. 3a illustrates such VNS pulse bursts Si, each including of a plurality of a number of 900 (30 Hz×30 seconds) individual pulses I, in the above example. The pulses have the same amplitude and the same width, so that all the pulses individually deliver the same VNS stimulation energy. Furthermore, also in this example, the interval between two successive pulses I of the same burst is a constant interval.

The invention proposes to modulate the energy of the bursts successively applied to the vagus nerve in deciding, for each burst, to deliver a variable number of the pulses initially envisaged.

This technique is implemented by block 20 of FIG. 2, which schematically and symbolically shows the functions implemented by the invention, preferably implemented in practice as a routine of the control software of the device.

The modulation circuit 20 includes a binary pseudo-random generator 22 of the "heads or tails" type, thus providing at the output for each applied VNS pulse, a value of '0' or '1' which will control the respective inhibition or authorization of the delivering of the VNS pulse, for each pulse I of each of the successive bursts Si (function schematized by the AND gate 24).

The "heads or tails" function can be obtained, for example, with an algorithm for pseudo-random selection of a number of N bytes, the "heads" being represented by the value '0' of a predetermined bit of this number and the "tails" by the value '1' of the same bit of the same number.

One can for example use an iterative algorithm defining a sequence S such that $S_{n+1}=(S_n*16807)$ modulo 4294967296, with $S_0$ arbitrarily chosen, $S_o$ being for example a value representing the internal clock of a system or a combination of this internal clock and of another time-dependent parameter. The result '0' or '1' of the (n+1)th rank will be the value of one of any of the predetermined bits of $S_{n+1}$.

Figure 3B:
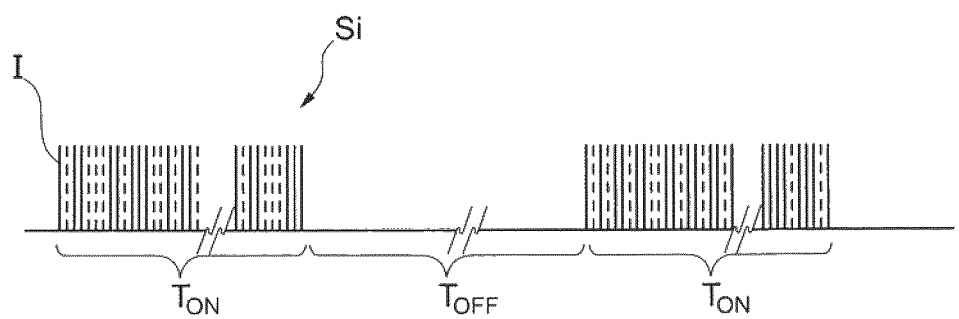

The result of this stochastic modulation function with inhibition/authorization of the delivering of each of the pulses in each burst is shown in FIG. 3b, with bursts whose delivering was inhibited compared to FIG. 3a shown in dashed lines.

The energy delivered to each burst Si will thus totally and unpredictably vary, between a theoretical minimum and a theoretical maximum:

The minimum corresponds to a zero energy situation wherein all pulses of the burst were inhibited; and The maximum corresponds to the case wherein no pulse would have been inhibited.

Figure 3C:
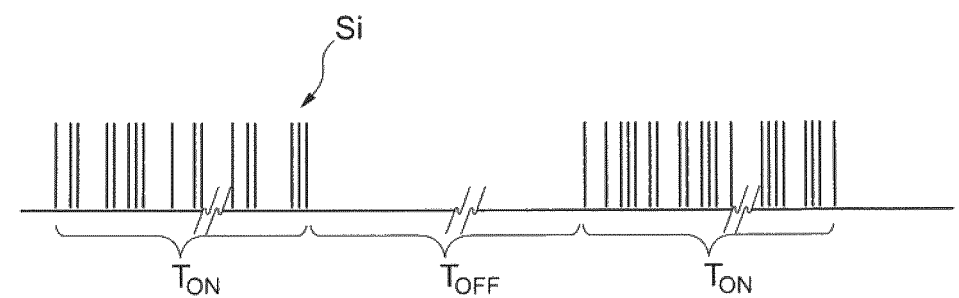

Thus, it can be observed, as shown FIG. 3c, a high variability induced from one burst to the next, of the interval between the actually delivered successive pulses, and the overall stimulation energy delivered by the burst, making it impossible or at least very difficult, to create a physiological control loop which would oppose to the neuronal therapy that is to be applied to the patient.

The invention claimed is:

1. An active implantable medical device for neuronal therapy by vagus nerve stimulation (VNS) including:
    a generator that produces bursts of N VNS stimulation pulses generated in succession during the respective periods of activity, the periods of activity being separated by intermediate periods of inactivity during which no stimulation is delivered;
    a lead coupled to the generator and used by the generator to deliver the bursts of VNS stimulation pulses; and
    a modulation circuit that provides stochastic modulation of the bursts by separately controlling the delivery of each of the N VNS pulses of each burst, so as to randomly vary the VNS stimulation energy contained in this burst and the interval between successive pulses and thus counteract the appearance of a physiological compensation loop.

2. The device of claim 1, wherein the modulation circuit that provides stochastic modulation comprises:

a binary pseudo-random generator of the "heads or tails" type, outputting a random binary outcome '0' or '1' for each VNS pulse to be applied.

3. The device of claim 1, wherein modulation circuit that provides stochastic modulation is configured to control the inhibition or authorization of the delivery of the VNS pulse based on a random binary generation outcome for each pulse of each of the successive bursts, so as to randomly vary the number of VNS pulses delivered in a burst.

4. The device of claim 1, wherein the respective amplitudes of the VNS pulses delivered by the generator are all equal.

5. The device of claim 1, wherein the respective widths of the VNS pulses delivered by the generator are all equal.

6. The device of claim 1, wherein a repetition frequency of the successive VNS pulses delivered by the generator in each burst is constant over the activity period, whether the delivery of these pulses by the generator is or is not inhibited by the modulation circuit.

7. The device of claim 6, wherein said repetition frequency of the VNS pulses delivered by the generator is between 15 and 50 Hz.

8. The device of claim 1, wherein a length of the activity periods (TON) is constant.

9. The device of claim 8, wherein the length of the activity periods (TON) is between 15 and 60 seconds.

10. The device of claim 1, wherein a duration of said inactivity periods (TOFF) is constant.

11. The device of claim 10, wherein the duration of said inactivity periods (TOFF) is between 2 and 10 minutes.

12. A method for providing neuronal therapy by vagus nerve stimulation (VNS), comprising:
producing, by a generator of an implantable medical device, bursts of a plurality of VNS stimulation pulses;
delivering, by a lead coupled to the generator, the bursts of the plurality of VNS stimulation pulses; and
applying, by a modulation circuit of the implantable medical device, stochastic modulation of the bursts by separately controlling the delivery of each of the VNS pulses of each burst to randomly or pseudo-randomly vary the VNS stimulation energy contained in this burst and the interval between successive pulses, counteracting the chance of creating a physiological compensation to the VNS.

13. The method of claim 12, wherein the bursts are provided in succession during different periods of heart activity, the periods of activity being separated by intermediate periods of inactivity during which no stimulation is delivered.

14. The method of claim 12, wherein the method is conducted by processor based control of a generator of an implantable device that conducts the VNS; and wherein the stochastic modulation comprises utilizing a binary pseudo-random generator of the "heads or tails" type that outputting a random binary outcome for each VNS pulse to be applied in a burst.

15. The method of claim 12, wherein the respective amplitudes of the VNS pulses delivered by the generator are all equal.

16. The method of claim 12, wherein the respective widths of the VNS pulses delivered by the generator are all equal.

17. The method of claim 12, wherein a repetition frequency of the successive VNS pulses (I) delivered by the generator in each burst is constant over the activity period, whether the delivery of these pulses by the generator is or is not inhibited by the modulation circuit.

18. The method of claim 17, wherein said repetition frequency of the VNS pulses delivered by the generator is between 15 and 50 Hz.

19. A device for providing heart health therapy by vagus nerve stimulation, comprising:
a lead having at least one electrode for applying pulses to the vagus nerve;
a generator configured to deliver a pulse burst using the lead and the electrode, wherein each burst comprises one or more pulses, wherein the generator has a stochastic modulation circuit that randomly inhibits or allows the delivery of each of the pulses of any one burst.

* * * * *